(12) United States Patent
Bödiger et al.

(10) Patent No.: US 6,320,016 B1
(45) Date of Patent: Nov. 20, 2001

(54) USE OF POLYCARBONATES CONTAINING IODINE PHENYL CARBONATE FOR PRODUCING SPECIAL SHAPED PARTS

(75) Inventors: Michael Bödiger, Dormagen; Wolfgang Ebert, Krefeld; Heinrich Alberts, Odenthal; Dieter Wittmann, Leverkusen; Thomas Eckel, Dormagen, all of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/445,716

(22) PCT Filed: Jun. 8, 1998

(86) PCT No.: PCT/EP98/03424

§ 371 Date: Dec. 9, 1999

§ 102(e) Date: Dec. 9, 1999

(87) PCT Pub. No.: WO98/59005

PCT Pub. Date: Dec. 30, 1998

(30) Foreign Application Priority Data

Jun. 20, 1997 (DE) .............................. 197 26 191

(51) Int. Cl.$^7$ ...................................... C08G 64/00
(52) U.S. Cl. ............................................. 528/198
(58) Field of Search ............................... 528/198

(56) References Cited

U.S. PATENT DOCUMENTS

| 3,028,365 | 4/1962 | Schnell et al. ................ 260/47 |
| 3,382,207 | 5/1968 | Jaquiss ....................... 260/45.7 |
| 3,409,704 | 11/1968 | Bailey ......................... 260/860 |
| 3,535,300 | 10/1970 | Gable ......................... 260/29.1 |

FOREIGN PATENT DOCUMENTS

| 1720812 | 7/1971 | (DE) . |
| 92/04392 | 3/1992 | (WO) . |

*Primary Examiner*—Terressa M. Boykin
(74) *Attorney, Agent, or Firm*—Joseph C. Gil; Aron Preis

(57) ABSTRACT

X-ray detectable molded articles prepared from polycarbonate resins are disclosed. The articles, preferably toys or medical equipment, are molded of polycarbonate the structure of which contains units derived from iodophenyl.

6 Claims, No Drawings

USE OF POLYCARBONATES CONTAINING IODINE PHENYL CARBONATE FOR PRODUCING SPECIAL SHAPED PARTS

The present invention relates to the use of polycarbonates containing iodophenyl carbonate in the production of special mouldings.

Within the scope of the present invention, polycarbonates containing iodophenyl carbonate are:

1. polycarbonates having a MW of from 3000 to 40,000 containing iodophenyl carbonate terminal groups,
2. polycarbonates of non-halogenated chain terminators having a MW of from 10,000 to 40,000 and containing diphenol-bis-iodophenyl carbonates,
3. polycarbonates of non-halogenated chain terminators having a MW of from 10,000 to 40,000 and containing bis-iodophenyl carbonate, and
4. mixtures of the polycarbonates according to 1) and the polycarbonates of non-halogenated diphenols and of non-halogenated chain terminators according to 2, or 3, variants 1, 2, 3 and 4 each having iodine concentrations of from 0.1 wt. % to 20 wt. %.

Special mouldings within the scope of the present invention are especially mouldings for medical applications, such as tubes or joint parts, and toys for children such as building bricks.

For the medical field and for children's toys, materials are sought which are as transparent as possible and have good mechanics, and which can be detected in the body in the course of X-ray examinations. Commercial moulding compositions based on polycarbonates are not suitable for that purpose, since their contrast in the X-ray image is too low. A material which is used for that purpose is, for example, PVC, whose plasticiser content is undesirable in the medical field and whose mechanical properties do not satisfy requirements. Known iodine-containing polymers also have only unsatisfactory mechanical properties and can be produced only with difficulty.

The object was, therefore, to develop moulding compositions which have good contrast in X-ray examinations while having good mechanical properties and high transparency and a glass temperature that is markedly greater than 100° C.

The major advantage of the mouldings according to the invention is that they have an improved X-ray contrast and are thus readily detectable and, accordingly, can be used successfully on the one hand in specific operations and on the other hand for remedying accidents caused by children swallowing toys.

U.S. Pat. No. 3,409,704 describes polycarbonates having iodophenyls as the terminal group (column 2, lines 60 ff).

U.S. Pat. No. 3,382,207 discloses iodine-containing diphenyl carbonates and their addition to polycarbonates.

According to DE-A 17 20 812, iodine-containing phenols are known as chain terminators for polycarbonates. See also the corresponding GB-B 11 63 816.

According to U.S. Pat. No. 3,535,300, iodine-containing compounds are known as additives to polycarbonates (column 4, line 64; column 5, line 43).

The use according to the invention and, accordingly, also the object cannot be taken from that prior art.

Polycarbonates according to 1) having $\overline{M}_w$ of from 3000 to 40,000 and containing iodophenyl carbonate terminal groups are preferably those having terminal groups of formula (I)

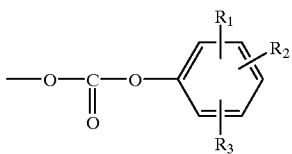

wherein
$R_1$ to $R_3$ represent H, optionally branched $C_1$–$C_{18}$-alkyl, Cl, Br or I, with the proviso that at least one of the radicals $R_1$, $R_2$ and $R_3$ represents I.

Preferred terminal groups are 4-iodophenyl carbonate and 2,4,6-triiodophenyl carbonate terminal groups.

Suitable diphenols for the preparation of the polycarbonates according to 1) are those of formula (II)

wherein
Z represents a divalent aromatic radical having from 6 to 30 carbon atoms.

Preferred diphenols are 1,1-bis-(4-hydroxyphenyl)-1-phenylethane, 1,1-bis-(4-hydroxyphenyl)-cyclohexane, 2,2-bis-(4-hydroxyphenyl)-propane and 1,1-bis-(4-hydroxyphenyl)-3,3,5-trimethylcyclohexane.

The polycarbonates according to 1) are either known or can be prepared by processes known from the literature; see, for example, the prior art cited above.

Preferred diphenol-bis-iodophenyl carbonates according to 2) are those of formula (III)

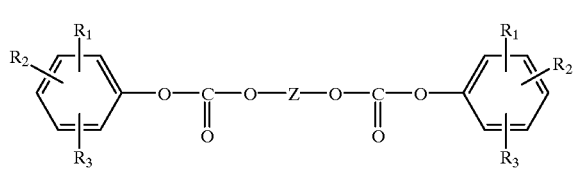

wherein
$R_1$, $R_2$ and $R_3$ are as defined for formulae (I) and (II).

Preferred bis-iodophenyl carbonates according to 3) are those of formula (IV)

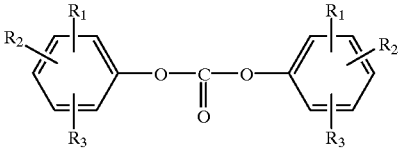

wherein
$R_1$, $R_2$ and $R_3$ are as defined for formula (I).

The diphenol-bis-iodophenyl carbonates according to 2) and the iodophenyl carbonates according to 3) are either known from the literature or can be prepared by processes known from the literature.

The conventional polycarbonates of non-halogenated diphenols and of non-halogenated chain terminators used as mixing partners in 2), 3) and 4) are likewise known or can be prepared by processes known from the literature (see, for example, U.S. Pat. No. 3,028,365).

The polycarbonates containing iodophenyl carbonate according to variants 1), 2), 3) or 4) to be used in accordance with the invention are to have iodine concentrations of from 0.1 wt. % to 20 wt. %, preferably from 1 wt. % to 15 wt. %, especially from 3 wt. % to 10 wt. %, in each case based on the total weight of variants 1), 2), 3) or 4).

Examples of the iodophenols (Ia)

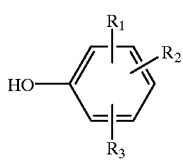

(Ia)

are 2-/3- or 4-iodophenol, 2-/3- or 4-iodo-6-methylphenol, 4- or 6-iodo-3-methylphenol, 2- or 6-iodo-4-methylphenol, 4,5-diiodo-2-methylphenol, 4,6-diiodo-2-methylphenol, 4,5diiodo-3-methylphenol, 4,6-diiodo-3-methylphenol, 2,4,6-triiodophenol, preferably 4-iodophenol and 2,4,6-triiodophenol.

The iodophenols are compounds which are obtainable in the chemicals trade or are accessible in organic syntheses from aromatic intermediates, optionally via diazonium salts. They can be used individually or in combinations, optionally also in combinations with conventional chain terminators such as phenol, p-tert-butylphenol, hexylphenol, isooctylphenol or nonylphenol.

Both the polycarbonates containing iodophenyl carbonate according to 1) and the conventional polycarbonates used as mixing partners according to 2), 3) and 4) can be linear or branched in a known manner.

Suitable branching agents are triphenols, trimesic acid (trichloride), cyanuric acid trichloride and 3,3-bis-(3-methyl-4-hydroxyphenyl)-2-oxo-2,3-dihydroindole.

Both the polycarbonates containing iodophenyl carbonate according to 1) and the conventional polycarbonates used as mixing partners according to 2), 3) and 4) can be provided with additives customary for polycarbonates, such as thermostabilisers, mould release agents, stabilisers against γ and β radiation, and antistatics.

The polycarbonate variations 1), 2), 3) or 4) to be used in accordance with the invention are processed to mouldings in a known manner.

In the Examples which follow, $\eta_{rel}$ is measured in dichloromethane at 25° C. and a concentration of 0.5 wt. %.

EXAMPLES

Example 1

180 ml of dichloromethane and 25.3 ml of 6.5% sodium hydroxide solution are placed in a 1000 ml three-necked flask having a stirrer, thermometer and reflux condenser. 22.83 g of 2,2-bis-(4-hydroxyphenyl)propane are dissolved therein, with stirring, and 15.8 g of phosgene are then introduced in the course of 5 minutes. 1.32 g of 4-iodophenol are then added, the mixture is stirred for 5 minutes at room temperature, and 0.137 ml of N-ethylpiperidine is added. Stirring is carried out for one hour at room temperature and then the organic phase is separated off and washed with dilute acid. Washing is then carried out with demineralised water until the washing phases are virtually free of electrolyte. The organic phase is concentrated and dried for 16 hours at 80° C. in a vacuum drying cabinet under a water jet vacuum.

Yield: 26.3 g $\eta_{rel}$=1.199

Example 2

As Example 1, but 2.83 g of 2,4,6-triiodobenzene are used as the chain terminator instead of 4-iodophenol.

Yield: 28.7 g $\eta_{rel}$=1.174

Example 3

450 ml of dichloromethane, 19.8 g of pyridine and 44.0 g of iodophenol are placed in a 1000 ml three-necked flask having a stirrer, thermometer and reflux condenser. 35.3 g of bischlorocarbonic ester of 2,2-bis-(4-hydroxyphenyl) propane, dissolved in 200 ml of dichloromethane, are added dropwise, with stirring, in the course of 40 minutes. Stirring is carried out for one hour at room temperature and then the organic phase is washed with dilute acid. Washing is then carried out with demineralised water until the washing phases are virtually free of electrolyte. The organic phase is concentrated and dried for 16 hours at 50° C. in a vacuum drying cabinet under a water jet vacuum.

Yield: 64.0 g

Example 4

900 ml of dichloromethane, 19.8 g of pyridine and 94.4 g of 2,4,6-triiodophenol are placed in a 2000 ml three-necked flask having a stirrer, thermometer and reflux condenser. 35.3 g of bischlorocarbonic ester of 2,2-bis-(4-hydroxyphenyl)propane, dissolved in 200 ml of dichloromethane, are added dropwise, with stirring, in the course of 65 minutes. Stirring is carried out for 15 minutes at room temperature and then the organic phase is washed with dilute acid. Washing is then carried out with demineralised water until the washing phases are virtually free of electrolyte. The organic phase is concentrated and dried for 16 hours at 50° C. in a vacuum drying cabinet under a water jet vacuum.

Yield: 89.0 g

The polycarbonates containing iodophenyl carbonate obtained according to Examples 1 to 4 are shaped in an injection-moulding machine to form building bricks. The X-ray contrast of the mouldings is so great that they can be detected in the stomachs of children.

What is claimed is:

1. An X-ray detectable article molded from a thermoplastic composition comprising polycarbonate having in its molecular structure at least one unit derived from iodophenyl carbonate, said polycarbonate prepared from diphenols conforming to HO—Z—OH wherein Z denotes a divalent aromatic radical having 6 to 30 carbon atoms.

2. An x-ray detectable toy molded from a thermoplastic composition comprising polycarbonate having in its molecular structure at least one unit derived from iodophenyl carbonate, said polycarbonate prepared from diphenols conforming to HO—Z—OH wherein Z denotes a divalent aromatic radical having 6 to 30 carbon atoms.

3. An x-ray detectable medical equipment molded from a thermoplastic composition comprising polycarbonate having in its molecular structure at least one unit derived from iodophenyl carbonate, said polycarbonate prepared from diphenols conforming to HO—Z—OH wherein Z denotes a divalent aromatic radical having 6 to 30 carbon atoms.

4. A method of imparting of x-ray detectability to an article molded from a thermoplastic composition comprising using at least some polycarbonate resin having in its molecular structure at least one unit derived from iodophenyl carbonate, said polycarbonate prepared from diphenols conforming to HO—Z—OH wherein z denotes a divalent aromatic radical having 6 to 30 carbon atoms.

5. The method of claim 4 wherein the article is a toy.

6. The method of claim 4 wherein the article is medical equipment.

* * * * *